US010548650B2

(12) United States Patent
Biedermann et al.

(10) Patent No.: US 10,548,650 B2
(45) Date of Patent: Feb. 4, 2020

(54) BONE NAIL FOR THE HEEL

(71) Applicants: Lutz Biedermann, VS-Villingen (DE); Wilfried Matthis, Weisweil (DE); Tobias Hägle, Donaueschingen (DE); Kaj Klaue, Savosa (CH)

(72) Inventors: Lutz Biedermann, VS-Villingen (DE); Wilfried Matthis, Weisweil (DE); Tobias Hägle, Donaueschingen (DE); Kaj Klaue, Savosa (CH)

(73) Assignee: BIEDERMANN TECHNOLOGIES GMBH & CO. KG, Donaueschingen (DE)

( * ) Notice: Subject to any disclaimer, the term of this patent is extended or adjusted under 35 U.S.C. 154(b) by 0 days.

(21) Appl. No.: 14/080,778

(22) Filed: Nov. 14, 2013

(65) Prior Publication Data
US 2014/0142575 A1     May 22, 2014

Related U.S. Application Data

(60) Provisional application No. 61/726,388, filed on Nov. 14, 2012.

(30) Foreign Application Priority Data

Nov. 14, 2012 (EP) .................................... 12192674

(51) Int. Cl.
A61B 17/84     (2006.01)
(52) U.S. Cl.
CPC .................. *A61B 17/846* (2013.01)

(58) Field of Classification Search
CPC ... A61B 17/72; A61B 17/7266; A61B 17/746; A61B 17/7233; A61B 17/7225;
(Continued)

(56) References Cited

U.S. PATENT DOCUMENTS 5,035,697 A * 7/1991 Frigg ............................... 606/67
5,066,296 A * 11/1991 Chapman ........................ 606/64
(Continued)

FOREIGN PATENT DOCUMENTS

CN          2805702 Y      8/2006
CN       201642283 U      11/2010
(Continued)

OTHER PUBLICATIONS

European Search Report and Opinion issued by the EPO for EP 12192674.5 dated Mar. 22, 2013 (7 pages).
(Continued)

*Primary Examiner* — Tessa M Matthews
(74) *Attorney, Agent, or Firm* — Lewis Roca Rothgerber Christie LLP (57) ABSTRACT

A bone nail (1) for the heel includes: a front portion (2) determined for insertion into one or more bones (14, 15, 16) or bone fragments of the heel and having a tip (3), and an arc-shaped main portion (4) extending from the front portion (2) and having a rear end (5), wherein the main portion (4) includes a tapered shape such that a cross sectional diameter of the main portion (4) within at least one first section (20) increases towards the rear end (5). According to embodiments, a curvature of the arc-shaped main portion (4) includes a radius of curvature $r_c$ which amounts to at least 130 mm. According to other embodiments, the tapered shape is a conical shape.

25 Claims, 7 Drawing Sheets

(58) Field of Classification Search
CPC . A61B 17/744; A61B 17/742; A61B 17/7283; A61B 17/7216; A61B 17/1725; A61B 17/68; A61B 17/7208–7241; A61B 17/846
USPC .................................................. 606/62–64
See application file for complete search history.

(56) References Cited

U.S. PATENT DOCUMENTS

| | | | |
|---|---|---|---|
| 5,531,748 A * | 7/1996 | de la Caffiniere | 606/62 |
| 6,102,914 A * | 8/2000 | Bulstra et al. | 606/306 |
| 7,771,428 B2 * | 8/2010 | Siravo | A61B 17/72 606/62 |
| 2004/0049192 A1 * | 3/2004 | Shimizu | 606/62 |
| 2005/0055024 A1 | 3/2005 | James et al. | |
| 2006/0200141 A1 | 9/2006 | Janna et al. | |
| 2006/0241605 A1 | 10/2006 | Schlienger et al. | |
| 2007/0123878 A1 * | 5/2007 | Shaver | A61B 17/72 606/64 |
| 2008/0027559 A1 * | 1/2008 | Crowninshield | A61F 2/38 623/23.44 |
| 2008/0262496 A1 * | 10/2008 | Schlienger et al. | 606/62 |
| 2009/0248025 A1 * | 10/2009 | Haidukewych | A61B 17/744 606/67 |
| 2010/0010490 A1 * | 1/2010 | Brigido | A61B 17/1725 606/64 |
| 2010/0292722 A1 | 11/2010 | Klaue | |
| 2010/0305623 A1 * | 12/2010 | Klaue | 606/329 |
| 2011/0087228 A1 * | 4/2011 | Ferrante et al. | 606/64 |
| 2012/0143192 A1 * | 6/2012 | Watanabe et al. | 606/64 |
| 2013/0317502 A1 * | 11/2013 | Overes | 606/66 |

FOREIGN PATENT DOCUMENTS

| | | |
|---|---|---|
| JP | 56-109650 A | 8/1981 |
| JP | 2007-325901 A | 12/2007 |
| JP | 2012-130724 A | 7/2012 |
| WO | WO 80/00533 A1 | 4/1980 |
| WO | WO 2009/067831 A1 | 6/2009 |
| WO | WO 2011/072249 A1 | 6/2011 |
| WO | WO 2011/155931 A1 | 12/2011 |

OTHER PUBLICATIONS

Chinese Office action dated Oct. 31, 2016 for Application No. 201310556321.5, and English translation.
JP Office action for Application No. 2013-232925, dated Oct. 10, 2017 and English translation.

* cited by examiner

BONE NAIL FOR THE HEEL

CROSS-REFERENCE TO RELATED APPLICATIONS

The present disclosure claims the benefit of U.S. Provisional Patent Application Ser. No. 61/726,388, filed Nov. 14, 2012, the contents of which are hereby incorporated by reference in their entirety, and claims priority from European Patent Application EP 12192674.5, filed Nov. 14, 2012, the contents of which are hereby incorporated by reference in their entirety.

BACKGROUND

The invention relates to a bone nail for the heel. The invention particularly relates to a bone nail configured to perform an arthrodesis of bones or bone fragments of the hindfoot.

Document US 2006/0200141 A1 describes a bone nail having a straight uncurved and unbent shape that, when being inserted into the hindfoot, extends through the calcaneus, talus and tibia. In order to implant the nail, a straight bore is formed which extends almost vertically through the bones, wherein entry of the bore into the calcaneus is located on the plantar side of the bone. Due to this construction, nerves concentrated on the plantar side of the foot may be damaged such that the patient may suffer from pain due to the implant.

Document US 2006/0241605 A1 shows an intramedullary nail for the tibia with an overall length between 200 and 500 mm and a curved section having a radius of curvature in the range of 300 to 1.300 mm. Only a portion of the nail is curved, which portion basically follows the shape of the tibia marrow canal.

Document WO 2011/072249 A1 discloses an anchor fusion device that substantially combines a hindfoot nail with a tibia marrow nail. The nail may have a length of 300 mm and a portion extending through the tibia has a radius of curvature of about 1.5 m. At a transition region between the tibia and the talus, a sharp bending occurs in 3-dimensional space at an angle of about 10°-15° towards a longitudinal axis of a straight bore extending through the talus and calcaneus, which bore likewise opens towards the plantar side of the calcaneus. Therefore, this construction suffers from the same disadvantages as noted above.

Document WO 2009/067831 A1 proposes an arc-shaped bone nail for the hindfoot, which extends from an axial face of the calcaneus in an almost circular shape through the talus up into the tibia. The bone nail is curved and has a curvature radius of at least 130 mm. Transverse bores are provided along the length of the nail, and at a rear end an inclined bore extends from the rear end at an angle of 15° with respect to a central axis of the nail to an outer surface to allow locking the bone nail via a bone anchor in the calcaneus and talus against forces tending to loosen the nail. The corresponding locking screw has a shank and a head, the shank being formed with a bone thread from the tip of the screw up to the head. The bone nail may have a rounded tip with slits formed therein and a cross-sectional shape of the nail may vary along a front portion, whereas a cross-sectional diameter is substantially constant up to the rear end of the nail.

SUMMARY

It is an object to provide a bone nail for the heel, which improves the process of insertion of the nail into an arc-shaped bore formed in the bone material, or which improves the long-term stability and the integration of the implant within the bone tissue involved.

The object is solved by a bone nail for the heel comprising the features according to claim 1. Advantageous embodiments and aspects become apparent from the dependent claims.

A bone nail according to a present embodiment includes a front portion and a main portion. The front portion is determined to accomplish insertion into a bore formed into one or more bones or bone fragments of the heel or hindfoot. The front portion has a tip. The main portion extends from the front portion up to a rear end of the bone nail. A radius of curvature of the arc-shaped main portion includes a radius of curvature $r_c$, which amounts to at least 130 mm, which radius allows the bone nail to extend from an axial end face of the calcaneus through the calcaneus and talus up into the lower part of the tibia, when the bone nail is inserted into a respective bore formed through these bones.

Further, the main portion includes a tapered shape, according to embodiments in particular a conical shape, wherein a cross-sectional diameter of the main portion increases towards the rear end in at least a (first) section thereof.

As a consequence, portions of the bone nail being first inserted into the bore include a comparatively small diameter increasing the ease of insertion into and guidance through the bore up into the lower part of the tibia.

Further, due to the tapered or even conical shape, the cross-sectional diameter of the bone nail passing a given location of the bore during insertion may smoothly increase such as to gradually widen the bore by softly compressing the adjacent bone tissue. Once the bone nail is fully inserted into the bore, a secure and stable fixation is achieved within the bore by, i.e., providing an interference fit of the nail with the surrounding bone tissue.

The expression "conically shaped" as used herein refers to a linear increase or decrease of diameters per unit length along central axis A. The expression "tapered" as used herein refers to smooth variations of the cross sectional diameter along the length direction of the central axis A, and encompasses a conical shape, but encompasses also curved shapes. A quantity expressed by "conicity" as used in the following is the amount of increase or decrease per unit length along the central axis A. The quantity "conicity" is also applicable where there is a tapered but non-conical shape, wherein this quantity then is local and varies along the central axis.

A locking bone anchor according to a specific embodiment is advantageous in conjunction with a bore of the bone nail, which extends from a rear end thereof towards an opening formed in an outer surface of the bone nail. The locking bone anchor has two thread sections: a (first) thread section provided adjacent an engagement portion of the anchor and a (second) thread section which corresponds to a bone thread. The first thread section may interact with an inner thread provided in the bore at the rear end of the nail, which allows to provide a fixed coupling of the locking bone anchor to the bone nail to prevent loosening thereof.

In a further embodiment, a closing cap may be provided which may cover a recess formed by the engagement portion. The closing cap seals the recess and the engagement portion in order to impede bone ingrowth or to prevent soft tissue to enter that recess, such that a correction or readjustment of a seat of the anchor in the bone nail and in the bone may be facilitated after months or years.

BRIEF DESCRIPTION OF THE DRAWINGS

Further advantages and aspects will become apparent from the detailed description of embodiments taken in conjunction with the drawings. Therein.

DETAILED DESCRIPTION

An embodiment of a bone nail 1 for the heel used in conjunction with a locking bone anchor 7 is described with reference to FIGS. 1 to 10 and a method of using the same illustrated with reference to FIGS. 11 to 18. With respect to FIGS. 1 and 2, the bone nail 1 is shown which is configured to be used to perform arthrodesis of bones or bone fragments of the hindfoot, in particular mutual immobilization of the calcaneus, talus and tibia. A medical and technical background regarding this field of application is also provided in above referenced document WO 2009/067831 A1, which description is incorporated herein by reference and shall not be repeated herein.

Figure 1:
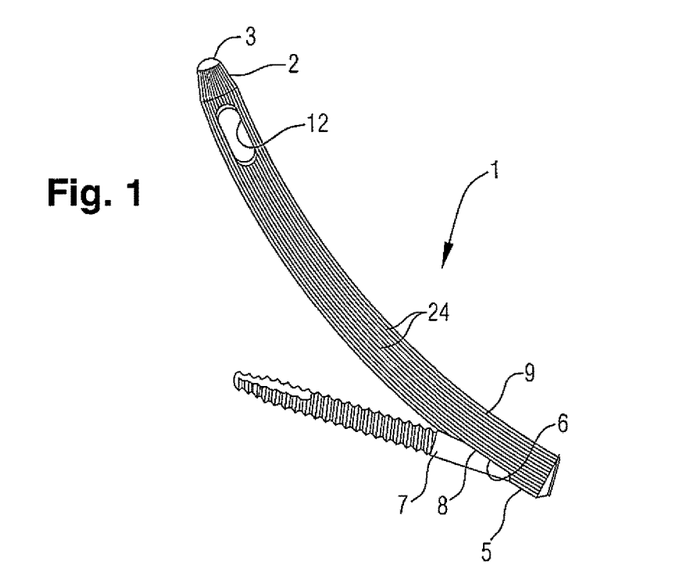
FIG. 1 shows a perspective view of the bone nail and a locking bone nacho according to an embodiment in an assembled state.
Figure 2:
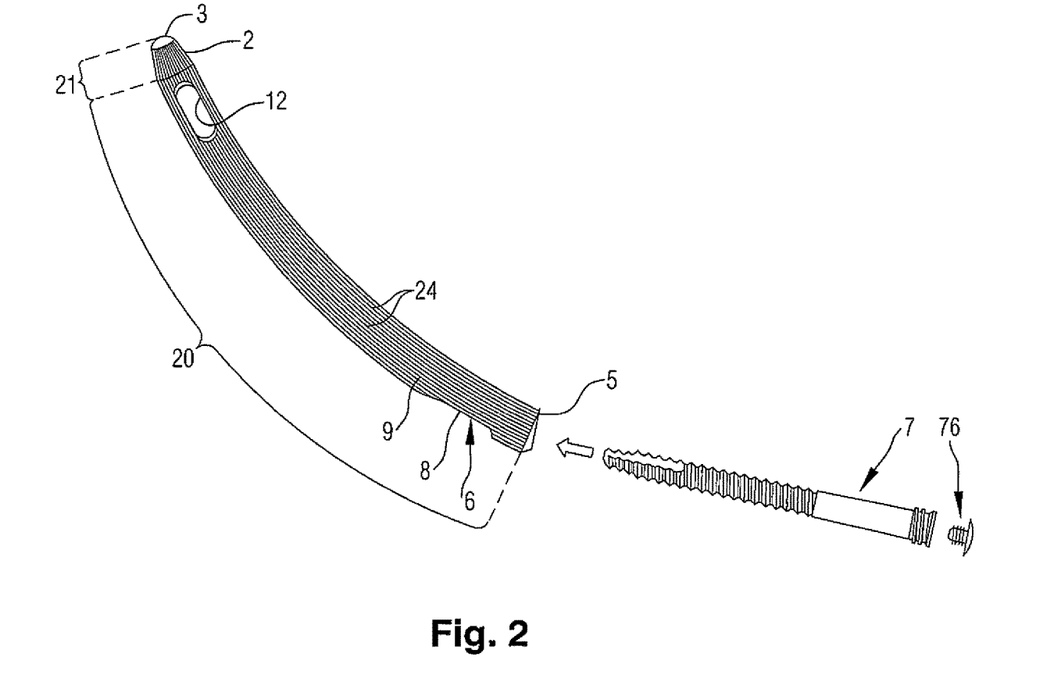
FIG. 2 shows the same as FIG. 1, but in an explosion view.
Figure 3:
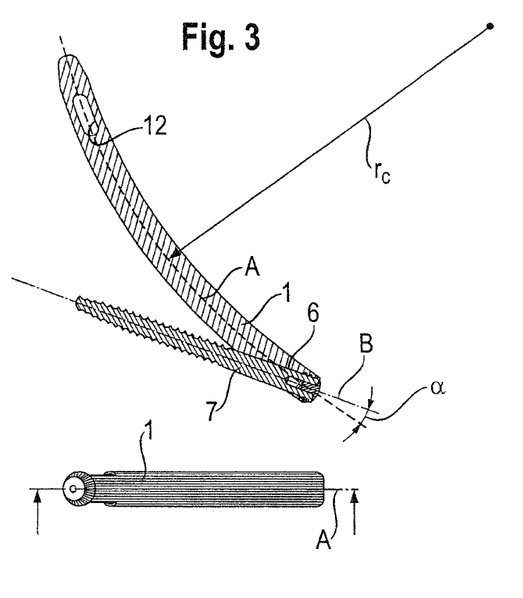
FIG. 3 shows the same as FIG. 1, but in a cross-sectional view.

The bone nail 1 includes a front portion 2 and a main portion 4. The main portion 4 represents the largest part of the bone nail 1 and extends from the front portion 2 up to the rear end 5 of the bone nail 1. As can be seen from the drawings, the main portion 4 is arc-shaped, and—as is depicted in FIG. 3—has a central axis A whose radius of curvature $r_c$ in this specific embodiment is constant along each infinitesimal section of the central axis.

The front portion 2 of this embodiment occupies a small portion of the bone nail 1 as compared with the main portion 4. The main portion has a first section 20, which in this embodiment is conically shaped and extends over the entire length of the main portion 4. The front portion 2 includes a rounded tip 3 and a second section 21, which in this embodiment is also conically shaped, see FIG. 2. The second conically shaped section 21 deviates from the first conically shaped section 20 of the main portion 4 in that its conicity, i.e., the variation of cross-sectional diameter per unit length, is larger than that a conicity of the second conically shaped section 21, respectively. This feature particularly allows an improved self-adjustment characteristic of the bone nail position within the bore during insertion, in particular during passage of the front portion at the transition between the talus and the tibia.

On the contrary, a conicity, i.e., variation of cross-sectional diameter per unit length, is comparatively small in the case of the first conically shaped section 20 of main portion 4. This allows a substantial contact of the outer surface 9 of main portion 4 with the surrounding bone tissue over substantially the entire length of the main portion 4. Upon insertion of the bone nail, the smooth variation of the cross-sectional diameter allows a controlled compression of the surrounding bone tissue and creating a stable and secure interference fit between the bone nail and the bone material.

In the specific embodiment shown, a diameter in a mid-portion of main portion 4 as measured along its entire length amounts to about 12 mm, while the corresponding diameter, at the transition to the front portion 2 amounts to 11.7 mm, whereas the corresponding diameter close to the rear end 5 amounts to 12.3 mm.

Nevertheless, typical diameters for the bone nail, more specifically as measured in its mid portion, range from 9 to 13 mm, but smaller or larger diameters than these may still be covered by the scope of embodiments. The above given conical tolerances of ±0.3 mm (−0.3 mm near front portion, +0.3 mm near rear end 5) from the reference value (12 mm in the embodiment at the mid portion) are also applicable to those other diameters given above (9 to 13 mm). Nevertheless, conical tolerances of ±0.6 mm or even up to ±0.9 mm, respectively, may still be within the scope of other embodiments. Note that if there is no clear transition between the front portion, or the tip, and the main portion, a point on the central axis A distant from the tip by a length amounting between one or two cross sectional diameters may be taken as a measure.

Regarding radii of curvature, it may be noted, that according to other embodiments, variations of the radius of curvature $r_c$ may vary along the central axis A. In this specific embodiment, the radius of curvature $r_c$ amounts to 200 mm. However, further embodiments of a bone nail allow for radii of curvature $r_c$ amounting to at least 130 mm, others to at least 140 mm, still others to at least 150 mm, and according to most specific embodiments, amount to at least 190 mm or at least 200 mm. The geometry selected depends on the specific conditions, which are individual for each patient.

Likewise, upper limits of the radius of curvature $r_c$ may amount to not more than 240 mm, preferably to 210 mm or less. A length of the bone nail as measured from the tip 3 to the rear end 5 amounts to at least 110 mm. According to other embodiments, the length for a bone nail 1 may amount to 125 mm or more, preferably 130 mm or more.

The circular arc, over which the bone nail 1 of specific embodiments may extend, may range from 38° to 70°, preferably from 48° to 55°. A maximum length of bone nail 1 may amount to 200 mm or less, preferably 160 mm or less. Specific embodiments reveal amounts of 150 mm or less.

It may be noted, that the main portion 4 may be partially curved, or may be curved with varying curvature, or may be curved with constant radius of curvature, as in the present embodiment. Likewise, the front portion 2 may continue to show the same curvature as the main portion 4, or may also vary in curvature, or may be formed in a straight, non-curved shape.

The outer surface 9 of the main portion 4 is further provided with a pattern of longitudinal grooves 24, which thereby form a groove-and-rib pattern, wherein the grooves are oriented parallel to the central axis A in order to allows and improve guiding of the bone nail 1 during insertion of the same into the bore of the hind-foot. This pattern further increases the surface area and allows an improved integration of the bone nail 1 within the growing bone tissue surrounding the nail once bone ingrowth into the grooves has started. Moreover, the groove and rib pattern oriented in this direction allows a larger amount of interference fit during insertion while the force needed is decreased.

The bone nail 1 comprises in the region of the main portion 4 a transverse bore 12 and a longitudinally inclined bore 6, which extends from the rear end 5 through the main portion 4 towards an opening 8 in the outer surface 9. As shown in FIG. 3 a locking bone anchor 7 is designed to be inserted into the bore 6, wherein said bore has a longitudinal axis B, that is inclined with respect to the central axis A of the main portion 4 by an angle α, which amounts to 0-20°, more preferably 10-20°. In this embodiment, the longitudinal axis B lies within the plane of curvature of the bone nail 1.

Figure 4:
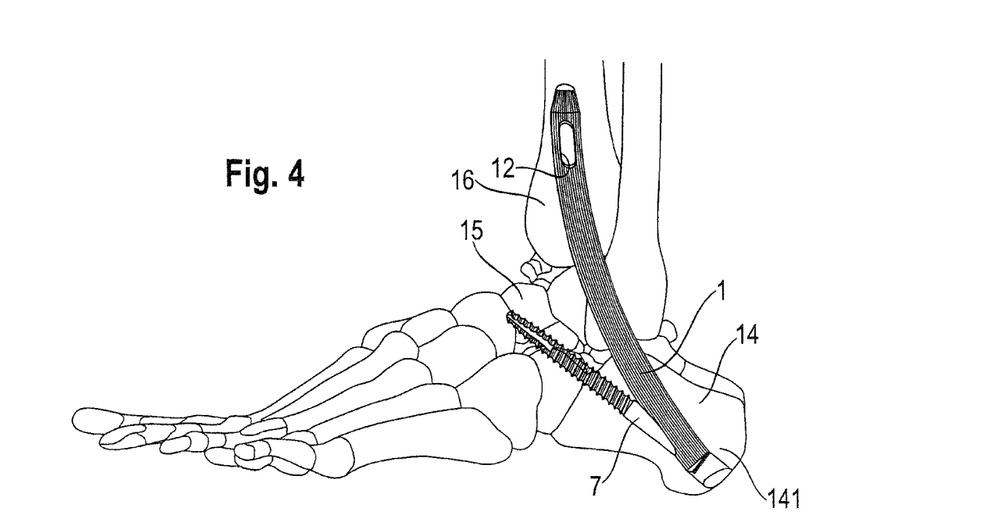
FIG. 4 shows the same as FIG. 1, but in an implanted state in the hindfoot.

As can be seen in FIG. 4, the locking bone anchor 7 is fixed through the calcaneus and talus thereby urging the bone nail further into the bore (not shown) due to its small inclination with respect to the central axis A, thereby preventing the bone nail 1 from loosening and falling-off from the bore. As can also be seen in FIG. 4, the bone nail 1 in its inserted state is accessible through an end face 141 of calcaneus 14 and extends further through the talus 15 into the tibia 16. Longitudinal bore 12 penetrating transversely through a region adjacent the front portion 2 of the bone nail 1 is designed to receive a second locking bone anchor (not shown) for further securing the nail in the tibia, wherein such fixation via bore 12 is only optional and depends on the circumstances.

Figure 5:
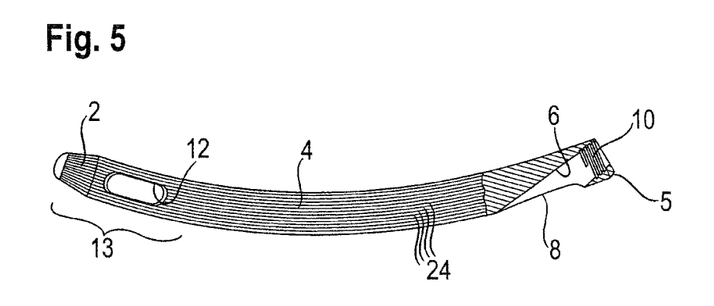
FIG. 5 shows the bone nail of FIG. 1 with a partial cross-sectional view of its rear end.
Figure 6:
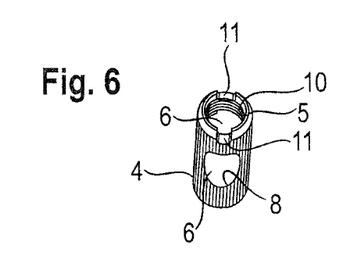
FIG. 6 shows a side view of the bone nail as seen from the right side of FIG. 5.

FIGS. 5 and 6 show more details of the main portion 4 close to the rear end 5. The first bore 6 further has an inner thread 10 close to its opening towards the rear end 5, and further has a flat surface towards the opening 8 in the outer surface 9 of the main portion 4.

The bone nail 1 of this embodiment is solid, i.e., basically non-tubular—except for the bores 6 and 12. Nevertheless, tubular shapes or channels provided within respective portions 2 or 4 may also be encompassed by other embodiments.

Figure 7:
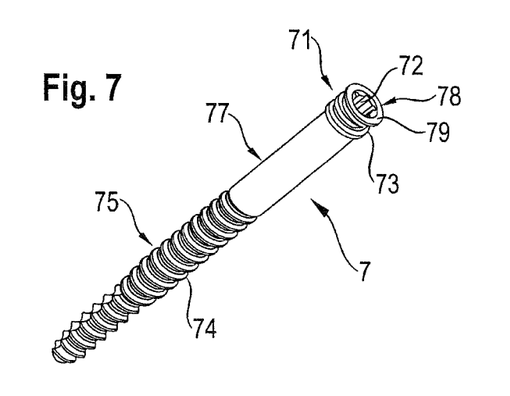
FIG. 7 shows a perspective view of the locking bone anchor shown in FIG. 1.
Figures 8, 9A, 9B:
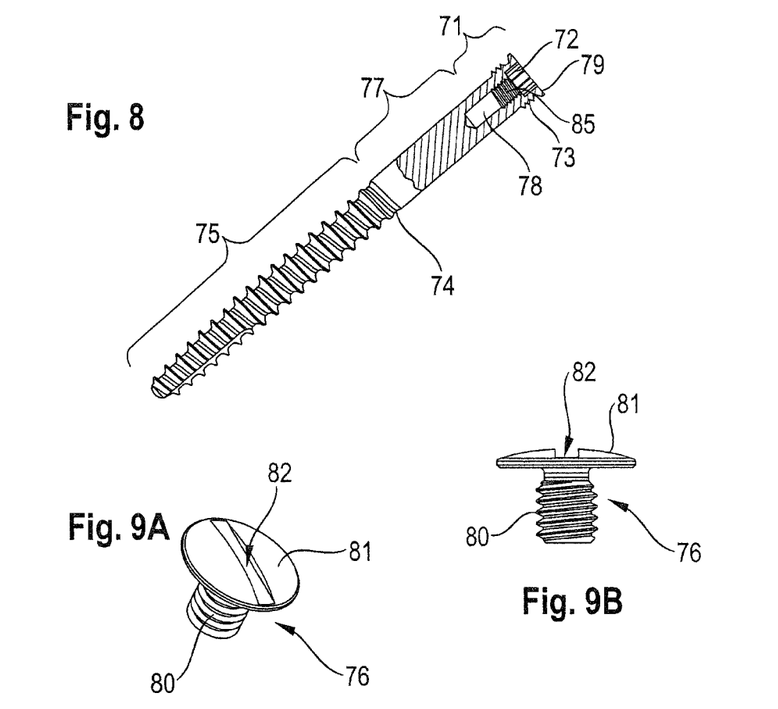
FIG. 8 shows the same as FIG. 7, but with a partial cross-sectional view of a head portion of the bone anchor.
FIG. 9A shows a perspective view of a closing cap.
FIG. 9B shows a side view of the closing cap.

Further details of the locking bone anchor 7 to be inserted into bore 6 of the bone nail 1 become apparent from FIGS. 7 and 8. The locking bone anchor 7 includes an engagement portion 72 for engagement with an external tool for screwing-in the locking bone anchor 7 into the bore 6 and the bone material of the calcaneus 14 and talus 15. In this example, a hexagon-shaped engagement portion 72 is used, but any other shapes of engagement portions are possible as well, e.g., star, polygon, etc.

The engagement portion 72 is provided as a recess 78 formed in an end face 79 of the bone anchor 7. The protruding edges of the end face 79 form an abutment for the locking bone anchor 7 at the rear end 5 of the main portion for the anchor 7. Adjacent the end face 79, a first outer thread section 73 is provided, which is configured to interact with the inner thread 10 formed in the bore 6 near the rear end 5 of the main portion 4 of bone nail 1. Adjacent the first outer thread section 73 a threadless section 77 extends preferably having a length such as to accomplish contact with the flat inner surface of the bore 6 provided in main portion 4. As a consequence of this plain contact between section 77 and bore 6 in growth of bone material into the bore 6 is advantageously impeded, which is useful, since during the lifetime of the implant, access and readjustment of the locking bone anchor 7 should be possible at any time.

Adjacent to the threadless section 77, a second outer thread section 75 extends up to the tip of the locking bone anchor 7. This section 75 forms the bone thread for fixing the bone anchor 7 in the surrounding bone material.

The threadless section 77 and the second outer thread section 75 together form a shank 74 of anchor 7, wherein an outer diameter of both sections 75, 77 is smaller than an outer diameter of the first outer thread section 73 such as to allow for insertion of these sections without screwing through the inner thread 10. Further, the thread lead of the second outer thread section 75 is larger than the thread lead of the first outer thread section 73 to provide self-locking of anchor 7. As shown in FIGS. 9A and 9B, a closing cap 76 is provided to cover and seal the recess 78, which includes the engagement portion 72.

For this purpose, the closing cap 76 is formed with a thread portion 80 and with a cap portion 81, wherein the thread portion 80 interacts with an inner thread 85 provided in a recess 78. By means of this closing cap, inward growth of bone tissue or soft tissue into the recess 78 is advantageously impeded allowing easy and less disruptive access to the bone anchor 7 at any time. The closing cap 76 may easily be attached and removed by means of an engagement portion 82.

Figure 10:
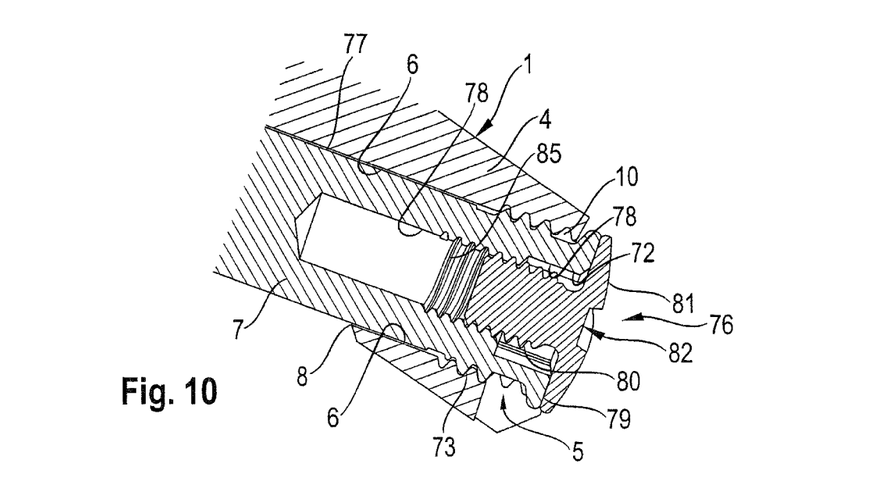
FIG. 10 shows an enlarged cross-sectional view of the rear end of the bone nail with locking bone anchor and the closing cap attached.

An overview of the mechanism provided by a corresponding head section of the bone anchor 7 in a state wherein it is installed to the bone nail 1 and closed by closing cap 76 is shown in FIG. 10.

The materials used for the bone nail 1, the locking bone anchor or the closing cap are preferable metals such as stainless steel, titanium, nickel titanium alloys, nitinol or the like. Other biocompatible materials are possible as well. All components are preferably made from rigid materials.

A process of implanting the bone nail 1 with the locking bone anchor 7 according to the above embodiment is depicted in FIGS. 11 through 18.

Figure 11:
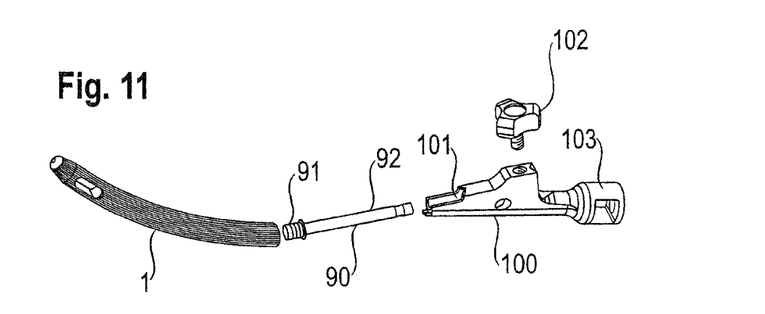
FIG. 11 shows a first step of mounting the bone nail to an adapter in a perspective view.
Figure 12:
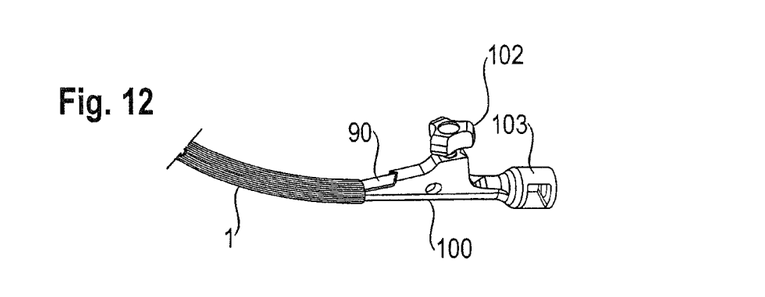
FIG. 12 shows a second step of mounting the bone nail to an adapter in a perspective view.

As shown in FIG. 11, the bone nail 1 without the locking bone anchor 7 is attached to an adapter 100 by means of a guiding pin 90. The guiding pin 90 has an outer thread section 91 configured to interact with the inner thread 10 at the rear end 5 of the bore 6. The other end section 92 of the guiding pin 90 is inserted into a receiving portion 101 of adapter 100 and locked by screw 102, as shown in FIG. 12.

Figure 13:
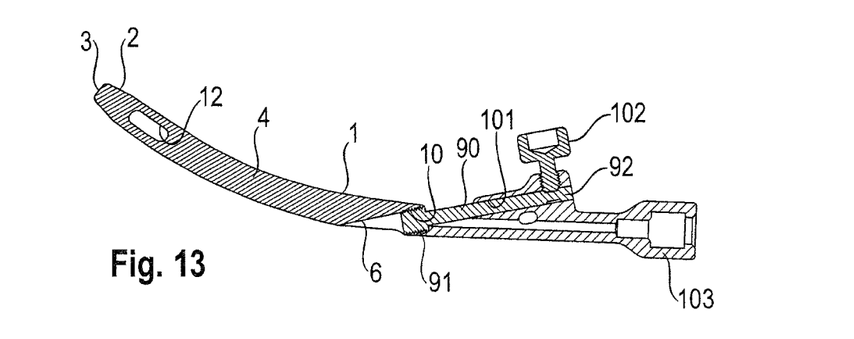
FIG. 13 shows a cross sectional view of the assembly shown in FIG. 12.
Figure 14:
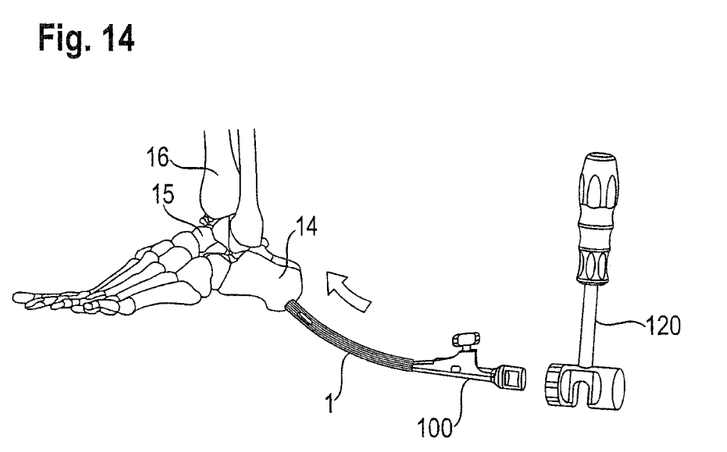
FIG. 14 shows the assembly of FIG. 12 in a step prior to inserting the bone nail into a bore already formed in the hindfoot.

FIG. 13 shows a cross-sectional view with details of the adapter 100 attached to the bone nail 1. As shown therein, the adapter 100 further comprises a head section 103 for receiving hammer strokes from a hammer 120, which is also shown in FIG. 14. Prior to inserting the connected assembly consisting of bone nail 1 and adapter 100, a circular arc-shaped bore 30 has been formed via the end face 141 of calcaneus 14 through the talus 15 into the tibia 16 by means of a targeting device not shown. The shape of the bore 30 is schematically indicated in FIG. 16 as described below.

Figure 15:
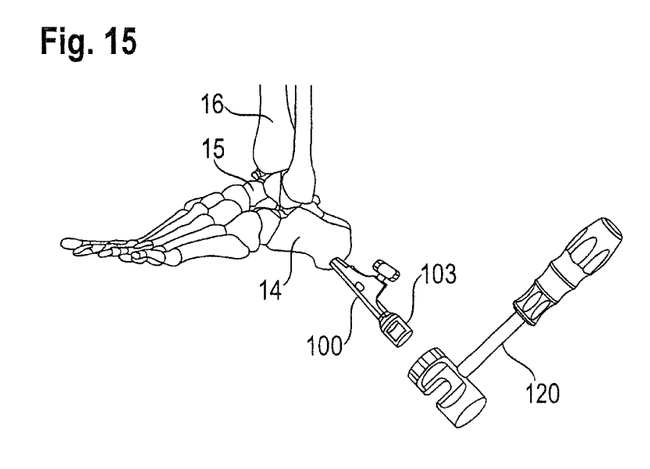
FIG. 15 shows the assembly of FIG. 12 in a step after the bone nail has been driven into the bore via a hammer.

As shown in FIG. 15, the bone nail 1 has been inserted in its entirety into the bore 30 by means of hammer strokes via hammer 120 such that only the adapter 100 protrudes from the opening of bore 30 in the axial end face of calcaneus 14. Next, the adapter 100 may be removed by loosening the screw 102, where after the pin 90 may be unscrewed from the inner thread 10 of the bore 6 of bone nail 1.

Figure 16:
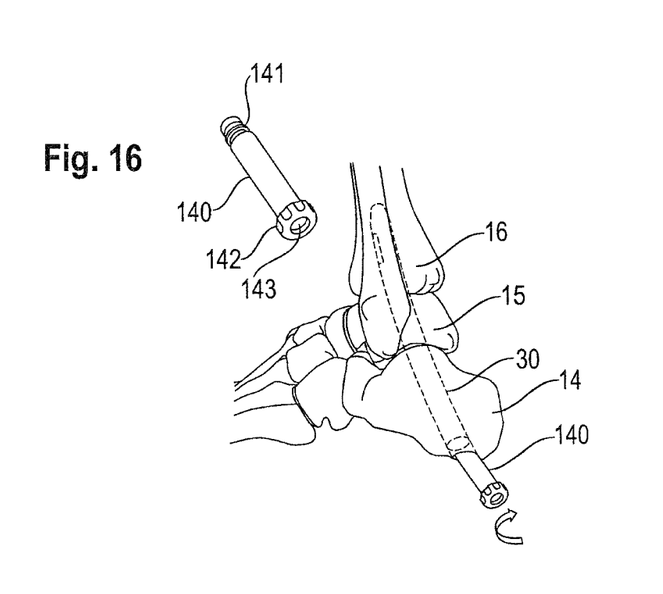
FIG. 16 shows a step of applying a drill jig pin to form a bore for receiving the locking bone anchor.
Figure 17:
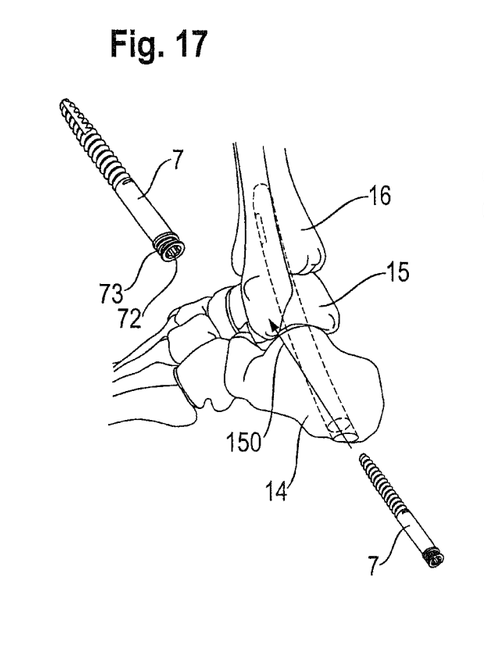
FIG. 17 shows a step of inserting the locking bone anchor.

As shown in FIG. 16, a drill jig pin 140 having a tubular portion 140, an engagement portion 142 and a thread portion 141 may be inserted into the opening of the end face 140 of calcaneus 14 and immediately thereafter into the bore 6 of bone nail 1. The outer thread portion 141 is threaded into inner thread 10 of bore 6. Then, the inner cylindrical bore 143 of drill jig pin 140 defines an axis 150 for a drill tool in order to form a straight bore for receiving the locking bone anchor 7, as can be seen in FIG. 17.

Figure 18:
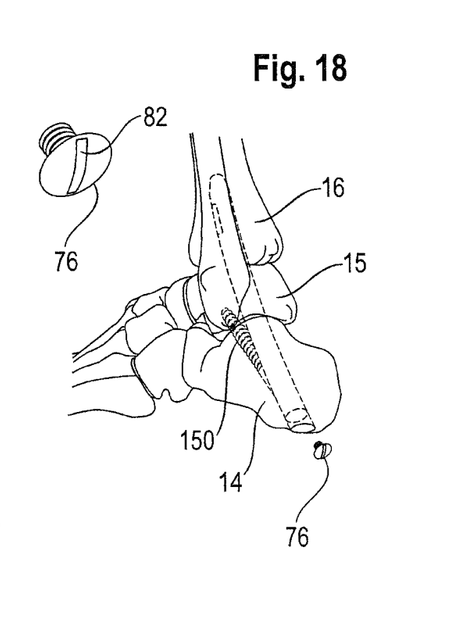
FIG. 18 shows a step of attaching a closing cap to cover a recess of an engagement portion positioned at the rear end of the bone nail, when the locking bone anchor is attached to the bone nail.

Thereafter, the drill jig pin 140 is removed and the locking bone anchor 7 is inserted and screwed into the bone and the inner thread 10. Finally, as shown in FIG. 18, the closing cap 76 is screwed with its thread portion 82 onto inner thread 85 formed within recess 78 of the bone anchor 7.

It may be noted that above embodiment depicts detailed features, whereas the person skilled in the art readily recognizes that further modifications may be made without departing from the scope as set forth in the appended claims.

For example, in the embodiments as illustrated above, the outer surface 9 of the main portion 4 and front portion 2 of bone nail 1 is formed with a pattern of grooves 24 and ribs there between. However, a smooth or otherwise structured surface may also be provided. Also alternating smooth regions and groove-and-rib patterns may be conceived.

Further, in the embodiments above, a conically shaped section 21 of front portion 2 is distinguished from the conically shaped section 20 of main portion 4 by an abrupt transition in conicity, i.e., increase of diameter per unit length. However, a smooth transition with continuously varying conicity between both regimes may also be realized.

In the above embodiments, substantially the entire length of the bone nail 1 is provided with some degree of conicity. However, it is also possible to apply a conical or curved shape only in a partial section, or in partial sections with regions of constant diameter arranged there between.

In some of the above embodiments, the front portion 2 has a rounded tip 3 and a conically shaped portion 21. However, according to other embodiments, the conically shaped portion may also be tapered but non-conical, or may even be fully omitted such that the tip portion has a direct transition to the main portion, which has the tapered or even conical section.

Further, the tip may not necessarily have a purely rounded shape. For example, the tip may be formed by a flat surface. Alternatively, the tip may also comprise multiple small flat surfaces arranged side by side to mimic a common obtuse tip.

The invention claimed is:

1. A bone nail for a heel comprising:
   a front portion configured for insertion into one or more bones or bone fragments of the heel and having a tip; and
   an arc-shaped main portion extending from the front portion to a rear end face opposite the front portion, wherein the main portion has a correspondingly arc-shaped longitudinal axis that extends through the front portion and the rear end face, and an outer surface that extends axially from the rear end face towards the front portion, and wherein the main portion is longer axially than the front portion;
   wherein the main portion defines a bore extending from a first opening formed in the rear end face to a side opening formed in the outer surface of the main portion, wherein the bore forms a substantially straight pathway from the first opening to the side opening to receive a bone anchor entirely therethrough;
   wherein the main portion has a tapered shape, such that a cross sectional diameter of the main portion continuously increases from the front portion to the side opening formed in the outer surface of the main portion, and wherein the main portion is arc-shaped from the front portion to the side opening formed in the outer surface of the main portion; and
   wherein at least seven longitudinal grooves extending parallel to the longitudinal axis are formed on the outer surface of the main portion and are separated from each other in a circumferential direction by respective ribs, and wherein the grooves cover a majority of the outer surface of the main portion, such that most of the outer surface of the main portion is recessed radially relative to the ribs.

2. The bone nail according to claim 1, wherein the tapered shape of the main portion is a conical shape.

3. The bone nail according to claim 1, wherein a curvature of the arc-shaped main portion includes a radius of curvature $r_c$ which amounts to at least 130 mm.

4. The bone nail according to claim 3, wherein the radius of curvature $r_c$ amounts to 240 mm or less.

5. The bone nail according to claim 1, wherein the cross-sectional diameter of the main portion continuously increases along an entire length of the main portion from the front portion to a location entirely past the side opening and wherein the main portion is arc-shaped from the front portion to a location entirely past the side opening.

6. The bone nail according to claim 1, wherein the front portion has a section comprising a tapered shape.

7. The bone nail according to claim 6, wherein the front portion further comprises an adjacent portion that is longer than the tip, and wherein the tapered shape of the front portion continuously extends from the tip to the main portion.

8. The bone nail according to claim 7, wherein the tapered shaped of the front portion tapers differently than the tapered shape of the main portion.

9. The bone nail according to claim 6, wherein a cross-sectional diameter of said front portion tapered shape continuously increases in a direction toward the main portion, and wherein a variation of cross-sectional area of said front portion tapered shape per unit length is greater than a variation of cross-sectional area of said main portion tapered shape per unit length.

10. The bone nail according to claim 1, wherein the tip of the front portion is provided with a rounded shape.

11. The bone nail according to claim 1, wherein an entire length from the tip up to the rear end face amounts to at least 110 mm.

12. The bone nail according to claim 1, further comprising an inner thread formed in the bore near the rear end face, and a locking bone anchor for locking the bone nail, the locking bone anchor having an engagement end provided with an engagement portion for receiving an engagement tool and a first outer thread section configured to interact with the inner thread and having a first diameter, and a shank provided with a second outer thread section to be screwed into bone material and having a second outer diameter smaller than the first diameter.

13. The bone nail according to claim 12, wherein a threadless section extends between the first and second outer thread sections of the locking bone anchor.

14. The bone nail according to claim 12, further comprising a cap for covering said engagement portion.

15. The bone nail according to claim 1, wherein the tip is curved along a central longitudinal axis of said front portion.

16. The bone nail according to claim 1, wherein the main portion is circular in cross-section.

17. The bone nail according to claim 1, wherein each of said grooves defines a U-shaped surface in cross-section as viewed along a plane perpendicular to a longitudinal axis of said groove.

18. The bone nail according to claim 1, further comprising a transverse bore in the main portion adjacent the front portion.

19. The bone nail according to claim 1, further comprising a bone anchor to lock the bone nail, a shaft of the bone anchor configured to enter the bore at the rear end face and pass through the side opening to screw into bone material.

20. The bone nail according to claim 1, wherein at least ten longitudinal grooves separated from each other in the circumferential direction by respective ribs are formed on the outer surface of the main portion.

21. The bone nail according to claim 1, wherein at least one of the grooves has a constant depth as the groove extends axially along at least part of the outer surface of the main portion.

22. A method for installing a bone nail in a heel, the bone nail comprising a front portion configured for insertion into one or more bones or bone fragments of the heel and having a tip, and an arc-shaped main portion extending from the front portion to a rear end face opposite the front portion, wherein the main portion has a correspondingly arc-shaped longitudinal axis that extends through the front portion and the rear end face, and an outer surface that extends axially from the rear end face towards the front portion, wherein the main portion is longer axially than the front portion, wherein the main portion defines a bore extending from a first opening formed in the rear end face to a side opening formed in the outer surface of the main portion, wherein the bore forms a substantially straight pathway from the first opening to the side opening to receive a bone anchor entirely therethrough, wherein the main portion has a tapered shape, such that a cross sectional diameter of the main portion continuously increases from the front portion to the side opening formed in the outer surface of the main portion, wherein the main portion is arc-shaped from the front portion to the side opening formed in the outer surface of the main portion, wherein at least seven longitudinal grooves extending parallel to the longitudinal axis are formed on the outer surface of the main portion and are separated from each other in a circumferential direction by respective ribs, and wherein the grooves cover a majority of the outer surface of the main portion, such that most of the outer surface of the main portion is recessed radially relative to the ribs, the method comprising:
  drilling an arc-shaped bore into bones or bone fragments of the heel;
  attaching an adapter to an engagement structure near the rear end face of the main portion of the bone nail;
  hammering the adapter, to hammer the front portion and main portion of the bone nail into the bones or bone fragments, with a hammer such that the bone nail is inserted into the arc-shaped bore;
  removing the adapter from the bone nail; and
  attaching a locking bone anchor to the engagement structure after removing the adapter.

23. A bone nail for a heel comprising:
  a front portion configured for insertion into one or more bones or bone fragments of the heel and having a tip; and
  an arc-shaped main portion extending from the front portion to a rear end face opposite the front portion, wherein the main portion has a correspondingly arc-shaped longitudinal axis that extends through the front portion and the rear end face, and an outer surface that extends axially from the rear end face towards the front portion, and wherein the main portion is longer axially than the front portion;
  wherein the main portion defines a bore extending from a first opening formed in the rear end face to a side opening formed in the outer surface of the main portion, wherein the bore forms a substantially straight pathway from the first opening to the side opening to receive a bone anchor entirely therethrough; and
  wherein the main portion has a tapered shape, such that a cross sectional diameter of the main portion continuously increases from the front portion to the side opening formed in the outer surface of the main portion, wherein the main portion is arc-shaped from the front portion to the side opening formed in the outer surface of the main portion; and
  wherein the main portion includes at least two grooved regions separated from one another by a smooth region, each of the grooved regions having a plurality of longitudinal grooves extending parallel to the longitudinal axis on the outer surface of the main portion and separated from each other in a circumferential direction by respective ribs, and wherein in the grooved regions, the grooves cover a majority of the outer surface of the main portion such that most of the outer surface of the main portion is recessed radially relative to the ribs.

24. The bone nail according to claim 23, wherein at least one of the grooves has a constant depth as the groove extends axially along at least part of the outer surface of the main portion.

25. A system comprising:
  a bone nail for a heel comprising:
    a front portion configured for insertion into one or more bones or bone fragments of the heel and having a tip; and
    an arc-shaped main portion extending from the front portion to a rear end face opposite the front portion, wherein the main portion has a correspondingly arc-shaped longitudinal axis that extends through the front portion and the rear end face, and an outer surface that extends axially from the rear end face towards the front portion, and wherein the main portion is longer axially than the front portion;
    wherein the main portion defines a bore extending from a first opening formed in the rear end face to a side opening formed in the outer surface of the main portion, wherein the bore forms a substantially straight pathway from the first opening to the side opening to receive a bone anchor entirely therethrough, and wherein a first engagement structure is formed in the bore; and
    wherein the main portion has a tapered shape, such that a cross sectional diameter of the main portion continuously increases from the front portion to the side opening formed in the outer surface of the main portion, wherein the main portion is arc-shaped from the front portion to the side opening formed in the outer surface of the main portion;
a tool for facilitating implanting of the bone nail, the tool having a second engagement structure configured to engage the first engagement structure; and
a locking bone anchor for locking the bone nail when the bone nail is implanted, the locking bone anchor having a third engagement structure configured to engage the first engagement structure to fix the locking bone anchor to the bone nail.

* * * * *